US012215315B2

(12) United States Patent
Kim et al.

(10) Patent No.: US 12,215,315 B2
(45) Date of Patent: Feb. 4, 2025

(54) METHOD FOR MODIFYING TARGET NUCLEIC ACID IN GENOME OF CELL

(71) Applicant: INDUSTRY-ACADEMIC COOPERATION FOUNDATION, YONSEI UNIVERSITY, Seoul (KR)

(72) Inventors: Hyong Bum Kim, Seoul (KR); Hui Kwon Kim, Jincheon-gun (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 1016 days.

(21) Appl. No.: 17/271,971

(22) PCT Filed: Aug. 30, 2019

(86) PCT No.: PCT/KR2019/011166
§ 371 (c)(1),
(2) Date: Feb. 26, 2021

(87) PCT Pub. No.: WO2020/046047
PCT Pub. Date: Mar. 5, 2020

(65) Prior Publication Data
US 2021/0340528 A1    Nov. 4, 2021

(30) Foreign Application Priority Data

Aug. 31, 2018 (KR) .................. 10-2018-0103979
Jan. 2, 2019 (KR) .................. 10-2019-0000391

(51) Int. Cl.
C12N 15/11    (2006.01)
C12N 9/22     (2006.01)
C12N 15/90    (2006.01)

(52) U.S. Cl.
CPC ................ *C12N 15/11* (2013.01); *C12N 9/22* (2013.01); *C12N 15/907* (2013.01); *C12N 2310/20* (2017.05); *C12N 2800/80* (2013.01)

(58) Field of Classification Search
CPC ........ C12N 15/11; C12N 9/22; C12N 15/907; C12N 2310/20; C12N 2800/80; C12N 15/111; C12N 15/102; C12N 15/113
(Continued)

(56) References Cited

U.S. PATENT DOCUMENTS 10,450,584 B2   10/2019 Barrangou et al.
2017/0275648 A1  9/2017 Barrangou et al.

FOREIGN PATENT DOCUMENTS

WO   WO-2016033298 A1 *  3/2016  .......... C12N 15/102
WO   WO 2017/205290 A1   11/2017
(Continued)

OTHER PUBLICATIONS

Nishimasu H, Shi X, Ishiguro S, Gao L, Hirano S, Okazaki S, Noda T, Abudayyeh OO, Gootenberg JS, Mori H, Oura S, Holmes B, Tanaka M, Seki M, Hirano H, Aburatani H, Ishitani R, Ikawa M, Yachie N, Zhang F, Nureki O., Science. Sep. 21, 2018;361(6408): 1259-1262. Epub Aug. 30, 2018. (Year: 2018).*
(Continued)

*Primary Examiner* — Anne Marie S Wehbe
*Assistant Examiner* — Katie L Pennington
(74) *Attorney, Agent, or Firm* — Oblon, McClelland, Maier & Neustadt, L.L.P.

(57) ABSTRACT

Provided are: a method for modifying a target nucleic acid in the genome of a cell using a novel PAM sequence; and a cell in which a target nucleic acid in the genome is modified thereby. Accordingly, genome editing can be performed by targeting a position that could not be previously targeted as
(Continued)

a target for genome editing, and thus the range of applications of genome editing can be expanded.

4 Claims, 20 Drawing Sheets

Specification includes a Sequence Listing.

(58) Field of Classification Search
USPC .................. 536/24.31; 435/455, 463, 199
See application file for complete search history.

(56) References Cited

FOREIGN PATENT DOCUMENTS

| WO | WO 2018/156818 A1 | 8/2018 |
|----|-------------------|--------|
| WO | WO 2019/010559 A1 | 1/2019 |

OTHER PUBLICATIONS

Korean Office Action issued Jul. 21, 2021 in Korean Patent Application No. 10-2020-0123333 (with English translation), 10 pages.
Extended European Search Report issued Apr. 20, 2022 in European Patent Application No. 19854936.2, 6 pages.
Nishimasu, H., et al. "Engineered CRISPR-Cas9 nuclease with expanded targeting space", Science, vol. 361, No. 6408, Aug. 30, 2018 pp. 1259-1262, XP055578577.
International Search Report issued on Nov. 29, 2019 in PCT/KR2019/011166 filed on Aug. 30, 2019, 2 pages.
Hu et al., "Evolved Cas9 variants with broad PAM compatibility and high DNA specificity", Nature, 2018, vol. 556, No. 7699, pp. 1-28.
Hirano et al., "Structural Basis for the Altered PAM Specificities of Engineered CRISPR-Cas9", Molecular Cell, 2016, vol. 61, pp. 886-894 (10 total pages).
Kleinstiver et al., "Engineered CRISPR-Cas9 nucleases with altered PAM specificities", Nature, 2015, vol. 523, No. 7561, pp. 1-27.
Hu, "Directed evolution of Cas9 for mammalian genome editing", Harvard University, Apr. 2018, pp. 1-137 (149 total pages).

* cited by examiner

METHOD FOR MODIFYING TARGET NUCLEIC ACID IN GENOME OF CELL

TECHNICAL FIELD

The present invention relates to a genome editing method in a cell using a novel protospacer adjacent motif.

BACKGROUND ART

CRISPR-Cas9 system is the adaptive immune system found in bacteria and archaea and has been used for genome editing in various organisms and cells, including human cells. Due to a lack of a protospacer adjacent motif (PAM) available in a target DNA region, insufficient on-target activity, or off-target effects, the applications of CRISPR-Cas9 are often limited. The PAM sequence for *Streptococcus pyogenes* Cas9 (SpCas9), which is the most commonly used CRISPR nuclease, is 5'-NGG-3'. Other CRISPR nucleases that exhibit efficient activities in mammalian cells also recognize other PAMs in addition to NGG. Although variants of CRISPR nucleases targeting sequences not containing the PAM sequences have been developed, sequences not being targeted still exist.

Recently, xCas9 and SpCas9-NG, which can target sequences with non-NGG PAMs, have been developed (Hu, J. H. et al., Nature vol. 556, pp. 57-63 (2018)). xCas9 had a lower off-target activity compared with SpCas9. The xCas9 and SpCas9-NG activities were studied at only 20 and 69 endogenous human genomic sequences, respectively. An extensive investigation of target sequences has not been carried out.

Accordingly, to broaden the application range of the CRISPR-Cas9 system, it is necessary to investigate the xCas9 and SpCas9-NG PAM compatibility and activities at target sequences and discover a PAM sequence other than NGG.

DESCRIPTION OF EMBODIMENTS

Technical Problem

Provided is a method for modifying a target nucleic acid in the genome of a cell using a novel PAM sequence.

Provided is a cell in which a target nucleic acid in the genome is modified by the method for modifying a target nucleic acid in the genome of a cell using a novel PAM sequence.

Solution to Problem

A first aspect provides a method for modifying a target nucleic acid in the genome of a cell, the method comprising incubating: a target nucleic acid; a clustered regularly interspaced short palindromic repeats (CRISPR)-associated (Cas) nuclease or a variant thereof; and a guide RNA.

The cell may be a cell in vivo or an isolated cell. When the cell is a cell in vivo, the method may be carried out in vivo. When the cell is an isolated cell, the method may be carried out ex vivo or in vitro.

The cell may be a somatic cell, a germ cell, a stem cell, a cancer cell, or a cell line. The cell may be selected from the group consisting of a cancer cell, a stem cell, a vascular endothelial cell, a leukocyte, an immune cell, an epithelial cell, a germ cell, a fibroblast, a muscle cell, a myelocyte, an epidermal cell, an osteoblast, and a nerve cell. The cell may be a cell from animals, including humans, plants, bacteria, or fungi.

The genome means all of the genetic information possessed by an organism or a cell.

The target nucleic acid means a nucleic acid intended to be modified.

The method for modifying a target nucleic acid in the genome of a cell can also be called as genome editing.

The method comprises incubating: a cell comprising a target nucleic acid; a polynucleotide encoding a clustered regularly interspaced short palindromic repeats (CRISPR)-associated (Cas) nuclease or a variant thereof; and a guide RNA.

The target nucleic acid may comprise a protospacer adjacent motif (PAM) and a target sequence complementary to the guide RNA.

The protospacer adjacent motif (PAM) may be a nucleotide sequence recognized by the Cas nuclease in the target nucleic acid. The PAM may be selected from the group consisting of 5'-NA-3', 5'-NTG-3', 5'-GTH-3', 5'-VCGD-3', 5'-TCGDG-3', 5'-GGT-3', 5'-BGC-3', 5'-RTG-3', 5'-NYGG-3', 5'-AGCCA-3', 5'-CTGCA-3', 5'-TGTCA-3', 5'-GCGCA-3', 5'-GCGCT-3', 5'-GCGTT-3', 5'-AGCCC-3', 5'-CGTCA-3', 5'-GCGTA-3', 5'-AGCCG-3', 5'-GCGTC-3', 5'-AGTCA-3', 5'-AGCAC-3', and 5'-AGCTC-3'. In the nucleotide sequence, "A" means adenine (A); "G" means guanine (G); "C" means cytosine (C); "T" means thymine (T). "N" means adenine (A), guanine (G), cytosine (C), thymine (T), uracil (U), unidentified, or other nucleic acids. "H" means a base other than guanine (G) and may be adenine (A), cytosine (C), thymine (T), or uracil (U). "V" means a base other than thymine (T) and uracil (U) and may be adenine (A), guanine (G), or cytosine (C). "D" means a base other than cytosine (C) and may be adenine (A), guanine (G), thymine (T), or uracil (U). "B" means a base other than adenine (A) and may be guanine (G), cytosine (C), thymine (T), or uracil (U). "R" means purine and may be adenine (A) or guanine (G). "Y" means pyrimidine and may be cytosine (C), thymine (T), or uricil (U). The 5'-NA-3' is 5'-AA-3', 5'-GA-3', 5'-CA-3', or 5'-TA-3'. 5'-NTG-3' is 5'-ATG-3', 5'-GTG-3', 5'-CTG-3', or 5'-TTG-3'. 5'-GTH-3' is 5'-GTA-3', 5'-GTC-3', or 5'-GTT-3'. 5'-VCGD-3' is 5'-ACGA-3', 5'-ACGG-3', 5'-ACGT-3', 5'-GCGA-3', 5'-GCGG-3', 5'-GCGT-3', 5'-CCGA-3', 5'-CCGG-3', or 5'-CCGT-3'. 5'-TCGDG-3' is 5'-TCGAG-3', 5'-TCGGG-3', or 5'-TCGTG-3'. 5'-BGC-3' is 5'-GGC-3', 5'-CGC-3', or 5'-TGC-3'. 5'-RTG-3' is 5'-ATG-3' or 5'-GTG-3'. 5'-NYGG-3' is 5'-ACGG-3', 5'-ATGG-3', 5'-GCGG-3', 5'-GTGG-3', 5'-CCGG-3', 5'-CTGG-3', 5'-TCGG-3', or '5'-TTGG-3'. The PAM may be directly contiguous or continuous to the 3'- or 5'-end of the target sequence.

The Cas nuclease may be an endonuclease cleaving double strands of a nucleic acid. The Cas nuclease may be an RNA guided DNA endonuclease. The Cas nuclease may be a nuclease derived from a bacterium selected from the group consisting of *Streptococcus* sp., *Campylobacter* sp., *Legionella* sp., *Neisseria* sp., *Pasteurella* sp., *Francisella* sp., and *Prevotella* sp. The Cas nuclease may be a nuclease derived from a bacterium selected from the group consisting of *Streptococcus pyogenes*, *Streptococcus thermophilus*, *Streptococcus aureus*, *Campylobacter jejuni*, *Legionella pneumophila*, *Neisseria meningitidis*, *Pasteurella multocida*, *Francisella novicida*, and *Prevotella disiens*. The Cas nuclease may be Cas9, Cpf1, C2c1, C2c2, C2c3, Cas3, Cas5, Cas7, Cas8, or Cas10. The Cas9 is, for example, *Streptococcus pyogenes* Cas9 (SpCas9).

The variant of the Cas nuclease is a variant having the functions of the Cas nuclease. The variant of the Cas nuclease may be selected from the group consisting of xCas9, SpCas9-NG, Cas9 nickase, deactivated Cas9 (dCas9), and destabilized Cas9 (DD-Cas9).

The polynucleotide encoding the Cas nuclease or a variant thereof may be contained in a plasmid vector or a viral vector.

When the variant of the Cas nuclease is SpCas9-NG, the PAM may be a polynucleotide consisting of a nucleotide sequence selected from the group consisting of 5'-NA-3', 5'-NTG-3', 5'-GTH-3', 5'-VCGD-3', and 5'-TCGDG-3'. When the Cas nuclease is *Streptococcus pyogenes* Cas9 (SpCas9), the PAM may be a polynucleotide consisting of a nucleotide sequence selected from the group consisting of 5'-GGT-3', 5'-BGC-3', 5'-RTG-3', 5'-NYGG-3', 5'-AGCCA-3', 5'-CTGCA-3', 5'-TGTCA-3', 5'-GCGCA-3', 5'-GCGCT-3', 5'-GCGTT-3', 5'-AGCCC-3', 5'-CGTCA-3', 5'-GCGTA-3', 5'-AGCCG-3', 5'-GCGTC-3', 5'-AGTCA-3', 5'-AGCAC-3', and 5'-AGCTC-3'.

The term "guide RNA" refers to a polynucleotide that recognizes a target nucleic acid in a cell and cleaves, inserts, or links the target nucleic acid through genome editing. The guide RNA may comprise a sequence complementary to a target sequence in the target nucleic acid. The guide RNA may be a polynucleotide complementary to a nucleotide sequence having consecutive 2 to 24 nucleotides (hereinafter, referred to as "nt") in the 5'- or 3'-direction of the PAM in the target nucleic acid. The length of the guide RNA may be 17 nt, 18 nt, 19 nt, 20 nt, 21 nt, 22 nt, 23 nt, or 24 nt. The guide RNA may be a single-chain guide RNA (sgRNA). The sgRNA may comprise crRNA (CRISPR RNA) specific for the target nucleic acid sequence and/or tracrRNA with which the Cas nuclease forms a complex. The guide RNA may be contained in a plasmid vector or a viral vector.

The incubation may be introducing the polynucleotide encoding the Cas nuclease or a variant thereof, or the guide RNA into the cell comprising the target nucleic acid. The introduction may include integration, transformation, transduction, transfection, or combinations thereof. The introduction may be transient or stable.

The target nucleic acid can be recognized by a complex of the Cas nuclease or a variant thereof with the guide RNA.

The complex of the Cas nuclease or a variant thereof with the guide RNA may modify the target nucleic acid sequence-specifically. The modification may be insertion, cleavage, insertion, ligation, deamination, or combinations thereof. The cleavage may be double strand cleavage of genomic DNA. The cleavage may produce a blunt end or a sticky end. The modification may be cleavage of the target nucleic acid and insertion of a heterogeneous polynucleotide into a cleavage site. The heterogeneous polynucleotide may be inserted into the cleavage site in the genome via a homology-dependent method. The homologous dependent method may be homologous recombination or homology-directed repair (HDR).

The method may be carried out in vitro, ex vivo, or in vivo.

A second aspect provides a cell in which a target nucleic acid in the genome is modified by the method for modifying a target nucleic acid in the genome of a cell of the first aspect.

The cell, the genome, the target nucleic acid, and the modification are as described above.

Advantageous Effects

According to a method for modifying a target nucleic acid in the genome of a cell using a novel PAM sequence, and a cell in which a target nucleic acid in the genome is modified thereby, genome editing can be performed by targeting a position that could not be previously targeted as a target for genome editing, and thus the range of applications of genome editing can be expanded.

MODE OF DISCLOSURE

Hereinafter, the present invention will be described in more detail through Examples. However, these Examples are for exemplifying one or more embodiments, and the scope of the present invention is not limited to those Examples.

Example 1. Determination of xCas9, SpCas9-NG, and SpCas9 PAM Sequences

1. Preparation of the Plasmid Library Containing Guide RNAs, PAM Sequences, and Target Sequences First, to determine PAM sequences recognized by Cas nucleases, the present inventors requested Twist Bioscience Co. to prepare oligonucleotide libraries.

Figure 1A:
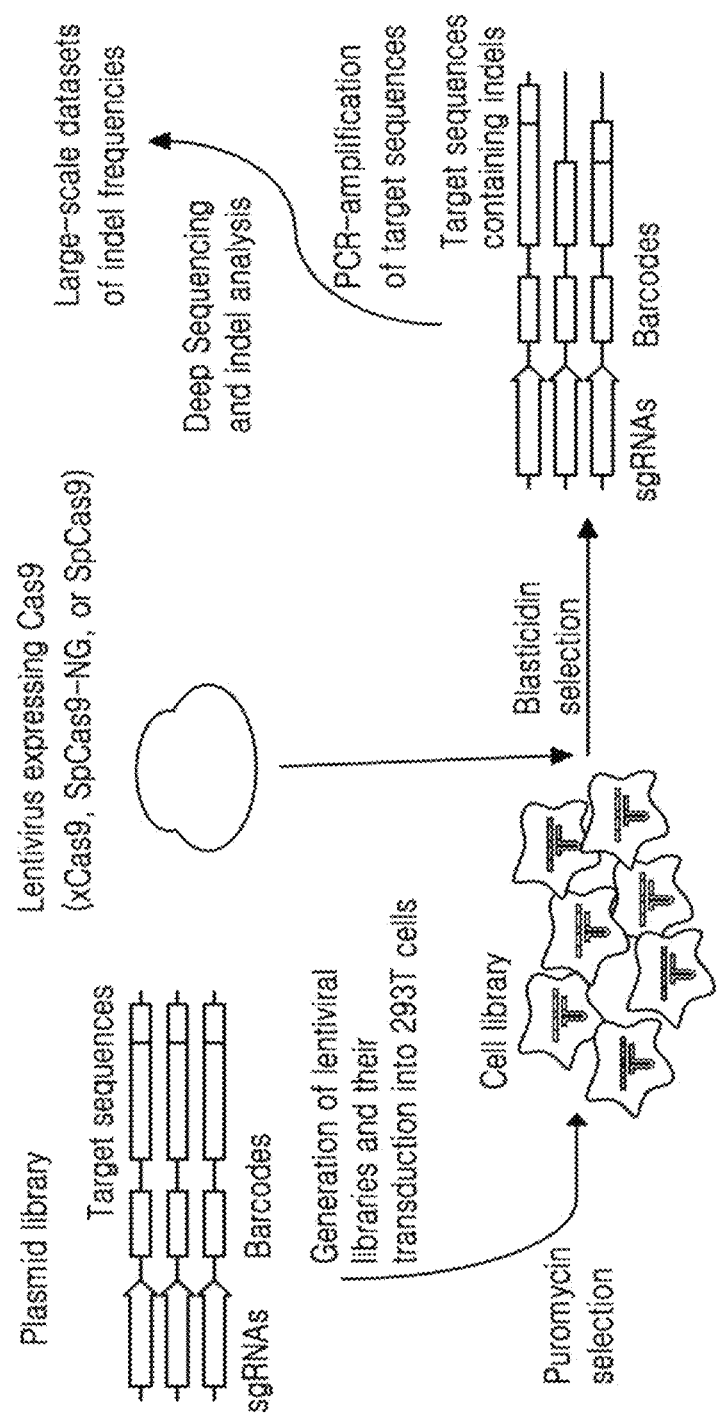
FIG. 1a is a schematic representation of experimentation on PAM sequence determination with fixed protospacers.
Figure 1B:
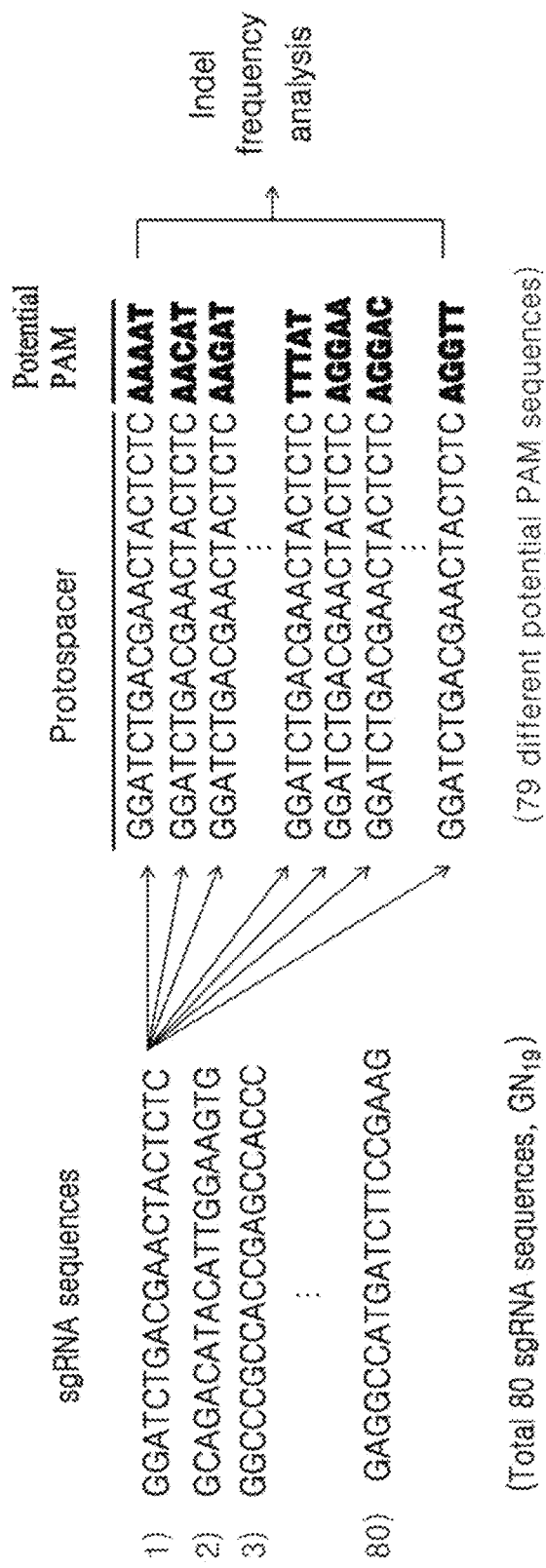
FIG. 1b is a schematic representation of an experimental design for PAM sequence determination.

Each oligonucleotide was designed to include a 19- or 20-nt sgRNA from the 5'-end, a BsmBI restriction site, barcode 1 (a 20 nt sequence), a second BsmBI restriction site, barcode 2 (a 15 nt sequence), and a 30-nt target sequence containing a PAM. Especially, oligonucleotides include 79 different 5-nt PAM sequences (64 from the NNNAT category+16 from the AGGNN category−1 redundant AGGAT) and 80 GN$_{19}$ single guide RNA (sgRNA) sequences, and thus the plasmid library targeting 6,320 (=79×80) target sequences was prepared (FIG. 1b).

The plasmid library containing sgRNAs and the target sequences was prepared using a two-step cloning process to prevent uncoupling between guide RNAs and target sequences during PCR amplification of the oligonucleotide pool.

The first step is preparing the initial plasmid library containing guide RNAs and the target sequences. BsmBI restriction enzyme (NEB) was used to linearize the Lenti-gRNA-Puro plasmid (Addgene, #84752). The PCR-amplified oligonucleotide pool (the target sequences) was ligated to the linearized vector. The reaction products were transformed into *E. coli*, and plasmids were separated from selected colonies. The primers used for amplification of the oligonucleotide pool are as follows:

```
Forward primer:
                                    (SEQ ID NO: 1)
5'-TTGAAAGTATTTCGATTTCTTGGCTTTATATATCTTGTGGAAAGGA
CGAAACACC-3'

Reverse primer:
                                    (SEQ ID NO: 2)
5'-GAGTAAGCTGACCGCTGAAGTACAAGTGGTAGAGTAGAGATCTAGT
TACGCCAAGCT-3'
```

The second step is inserting the sgRNA scaffold. The plasmid library prepared in the first step was digested with BsmBI restriction enzyme (NEB). After agarose electrophoresis, nucleic acid fragments were purified on a gel. An insert fragment containing the sgRNA scaffold was synthesized and cloned into a TOPO vector (T-blunt vector, Solgent). The sequence of the insert fragment is shown below. The sgRNA scaffold, including a poly T sequence, is shown in bold and the BsmBI restriction sites are underlined.

```
                                    (SEQ ID NO: 3)
5'-CGTCTCTGTTTTAGAGCTAGAAATAGCAAGTTAAAATAAGGCTAGT
CCGTTATCAACTTGAAAAAGTGGCACCGAGTCGGTGCTTTTTTGGGAGA
CG-3'
```

The TOPO vector containing the insert fragment was digested with BsmBI restriction enzyme (NEB) to isolate the 83-nt insert fragment. The insert fragment was ligated to the cut plasmid library. The product was transformed into *E. coli*, and the plasmid library was separated from selected colonies.

2. Preparation of Cell Library

First, for the production of lentivirus library, HEK293T cells, the human embryonic kidney cells, (ATCC) were prepared. The plasmids prepared in Example 1.1, psPAX2, and pMD2.G were mixed. HEK293T cells were transfected using Lipofectamine 2000 (Invitrogen). At 12 hours post-transfection, a fresh medium was added to the cells. At 36 hours post-transfection, the supernatant containing the virus was obtained. The obtained supernatant was filtered through Millex-HV 0.45 μm low-protein binding membrane (Millipore). Aliquots were stored at −80° C. until use. The virus yield was measured and verified with *Lenti*-X p24 rapid titer kit (Clontech). Serially diluted viral aliquots were transduced into HEK293T cells in the presence of 8 μg/ml polybrene. The cells were cultured in the presence of 2 μg/ml puromycin or 20 μg/ml blasticidin S (InvivoGen) to yield the virus titer.

For the transduction of the prepared lentivirus library, HEK293T cells were incubated overnight in culture dishes. The lentivirus library was transduced into the cells at a multiplicity of infection (MOI) of 0.3 in the presence of 8 μg/ml polybrene, after which the cells were incubated overnight. The cells were cultured in the presence of 2 μg/ml puromycin to remove the non-transduced cells. Cell libraries were maintained at $1.2 \times 10^7$ cells.

3. Cas9 Delivery into the Cell Library

Cell libraries at $1.2 \times 10^7$ cells were prepared and the xCas9-, SpCas9-NG-, or SpCas9-encoding viruses were transduced into the cells in the presence of 8 μg/ml polybrene. Transduction was performed at an MOI of 5. Cells were selected in the presence of 20 μg/ml blasticidin S.

4. Measurement of Indel Frequencies

To measure indel (insertion/deletion) frequencies in the genome of the cells prepared in Example 1.3, deep sequencing and analysis of indel frequencies were performed.

For deep sequencing, genomic DNA was isolated from the cells using Wizard Genomic DNA purification kit (Promega). The inserted target sequences were PCR amplified using 2× Taq PCR Smart mix (Solgent) for high-throughput experiment. For the first PCR, a total of 240 μg genomic DNA was used for each cell library to attain a coverage of more than 1000× over the library (about 10 μg genomic DNA per $10^6$ cells). 2.5 μg genomic DNA per reaction was subjected to the first PCR. All of the reaction products were pooled and then purified. 50 ng samples of the purified products were amplified by the second PCR using primers containing both Illumina adaptor and barcode sequences. The amplified products were subjected to electrophoresis and purification, followed by analysis using HiSeq or MiniSeq (Illumina).

The PCR primers used in the experiments are as follows:
Primers for the First PCR Reaction

```
Forward primers:
                        (Forward primer, SEQ ID NO: 4)
5'-ACACTCTTTCCCTACACGACGCTCTTCCGATCTCTTGAAAAAGTGG
CACCGAGTCG-3'

(SEQ ID NO: 5)
5'-ACACTCTTTCCCTACACGACGCTCTTCCGATCTTCTTGAAAAAGTG
GCACCGAGTCG-3'

(SEQ ID NO: 6)
5'-ACACTCTTTCCCTACACGACGCTCTTCCGATCTCGCTTGAAAAAGT
GGCACCGAGTCG-3'

Reverse primers:
                                    (SEQ ID NO: 7)
5'-GTGACTGGAGTTCAGACGTGTGCTCTTCCGATCTTTAAGTCGAGTA
AGCTGACCGCTGAAG-3'

(SEQ ID NO: 8)
5'-GTGACTGGAGTTCAGACGTGTGCTCTTCCGATCTATTAAGTCGAGT
AAGCTGACCGCTGAAG-3'

(SEQ ID NO: 9)
5'-GTGACTGGAGTTCAGACGTGTGCTCTTCCGATCTTATTAAGTCGAG
TAAGCTGACCGCTGAAG-3'
```

Primers for the Second PCR Reaction

```
    Forward primer:
                                    (SEQ ID NO: 10)
    5-AATGATACGGCGACCACCGAGATCTCAC (index)
    ACACTCTTTCCCTACACGAC-3'

Reverse primer:
                                    (SEQ ID NO: 11)
    5'-CAAGCAGAAGACGGCATACGAGAT (index)
    GTGACTGGAGTTCAGACGTGT-3'
```

To analyze indel frequencies, Python scripts were modified and used to analyze the deep sequencing data. A total of the 19-nt sequence consisting of the 15-nt barcode and 4-nt sequence located upstream of the barcode was used to identify each guide RNA and target sequence pair. Indels were considered to be xCas9-, SpCas9-NG-, or SpCas9-induced mutations when they were located at positions around the expected cleavage site (that is, the 8-nt region centered on the middle of that site). To eliminate background indel frequencies that were the result of array synthesis and PCR amplification, total read, indel read, and the indel frequency when Cas9 was not introduced were calculated and then the indel frequency (%) was calculated according to Equation 1 below:

$$\text{Indel frequency (\%)} = \frac{\text{Indel read} - (\text{The number of total read} \times \text{Background indel frequency})}{\text{Total read} - (\text{The number of total read} \times \text{Background indel frequency})} \times 100 \quad \text{(Equation 1)}$$

The deep-sequencing data were uploaded to the NCBI Sequence Read Archive (SRA; www.ncbi.nlm.nih.gov/sra/) under Accession No. SRP158724.

5. PAM Sequence Determination

From the deep sequencing data obtained according to Example 1.4, the PAM sequences having high indel frequency for xCas9, SpCas9-NG, or SpCas9 nucleases were selected.

The PAM sequences having an average indel frequency of 5% or higher by day 6 following the transduction into human cells were selected. Then, the indel frequencies were analyzed for xCas9, SpCas9-NG, and SpCas9 nucleases and the PAM sequences.

Figure 2A:
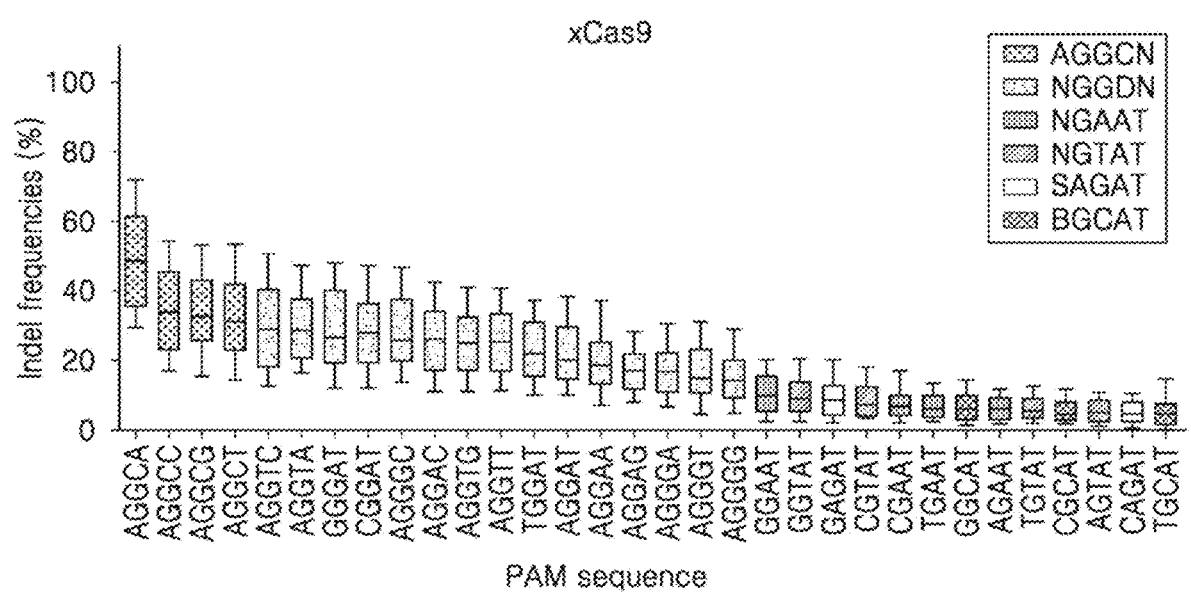
FIGS. 2a, 2b (right panel and left panel) and 2c are graphs showing indel frequencies (%) for PAM sequences for xCas9 nuclease.
Figure 2B:
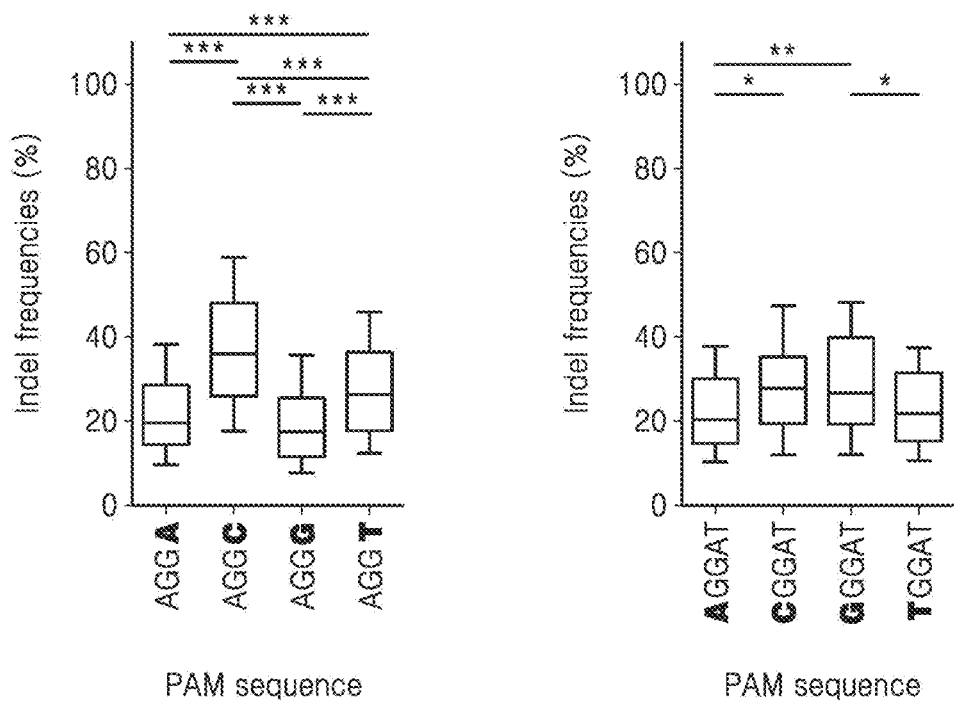
Figure 2C:
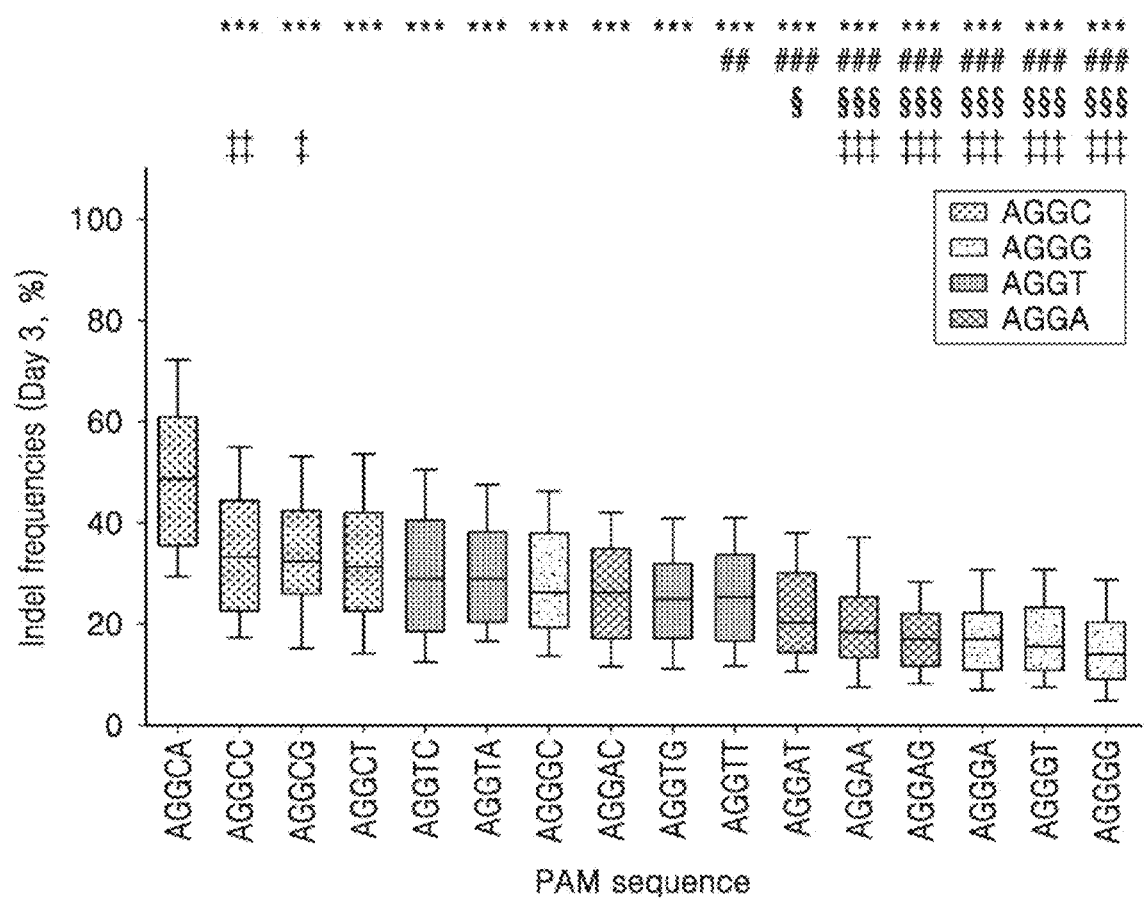
Figure 3A:
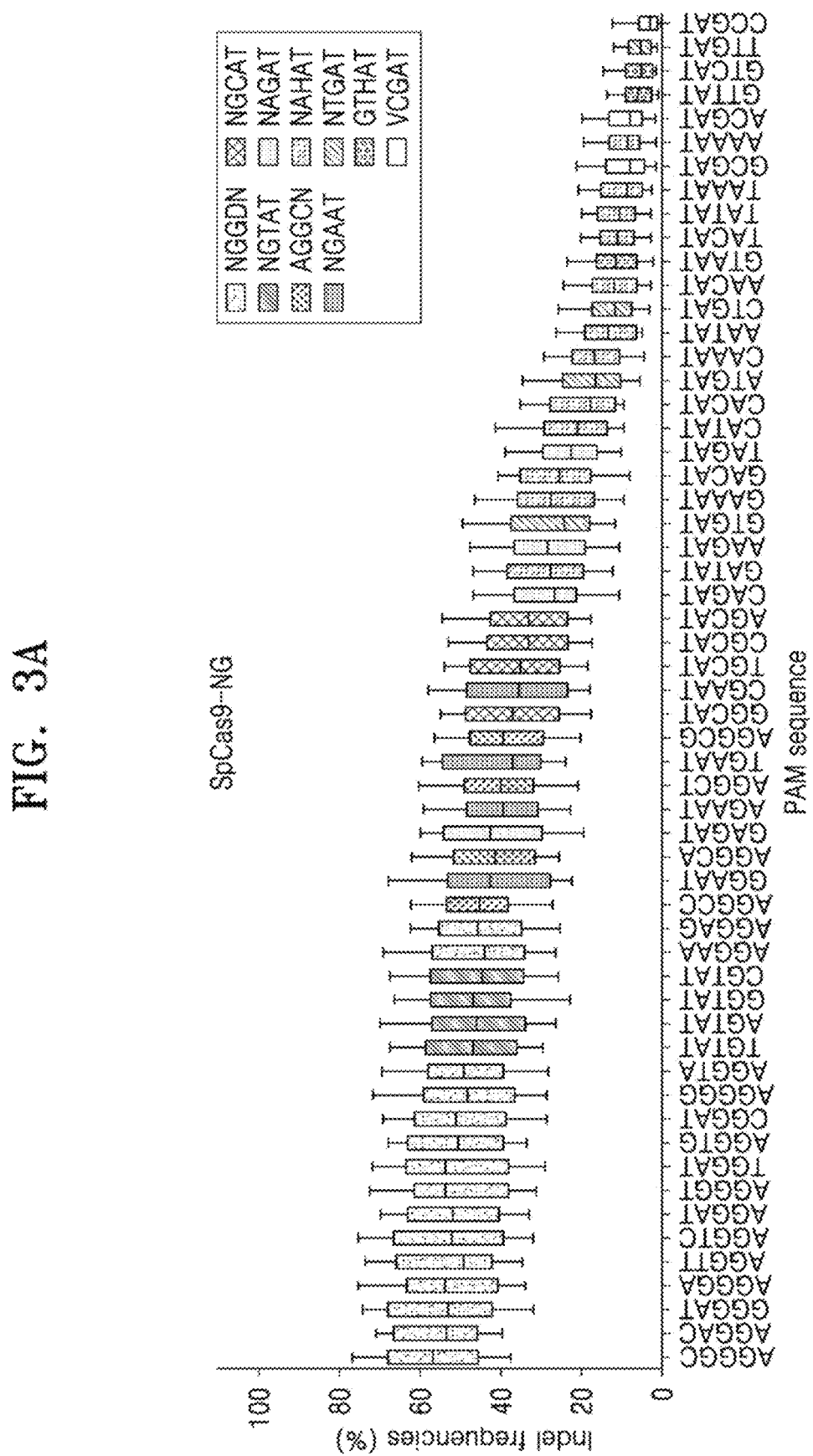
FIGS. 3a, 3b (right panel and left panel) and 3c are graphs showing indel frequencies (%) for PAM sequences for SpCas9-NG nuclease.
Figure 3B:
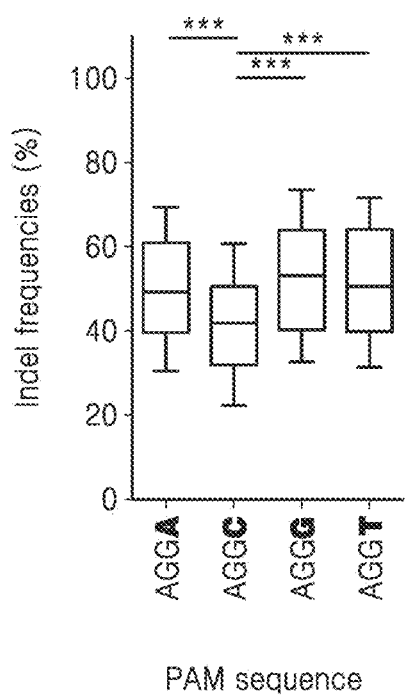
Figure 3B:
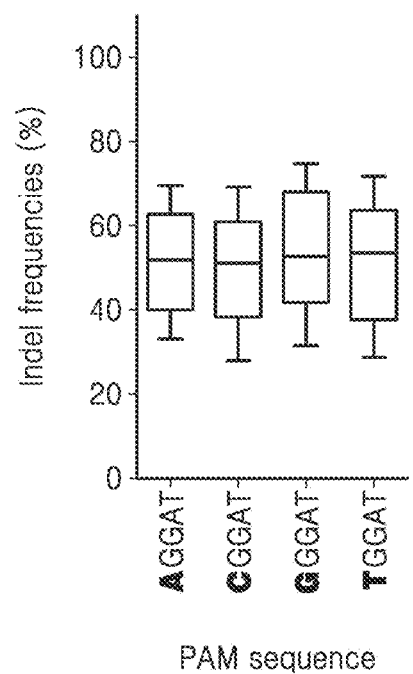
Figure 3C:
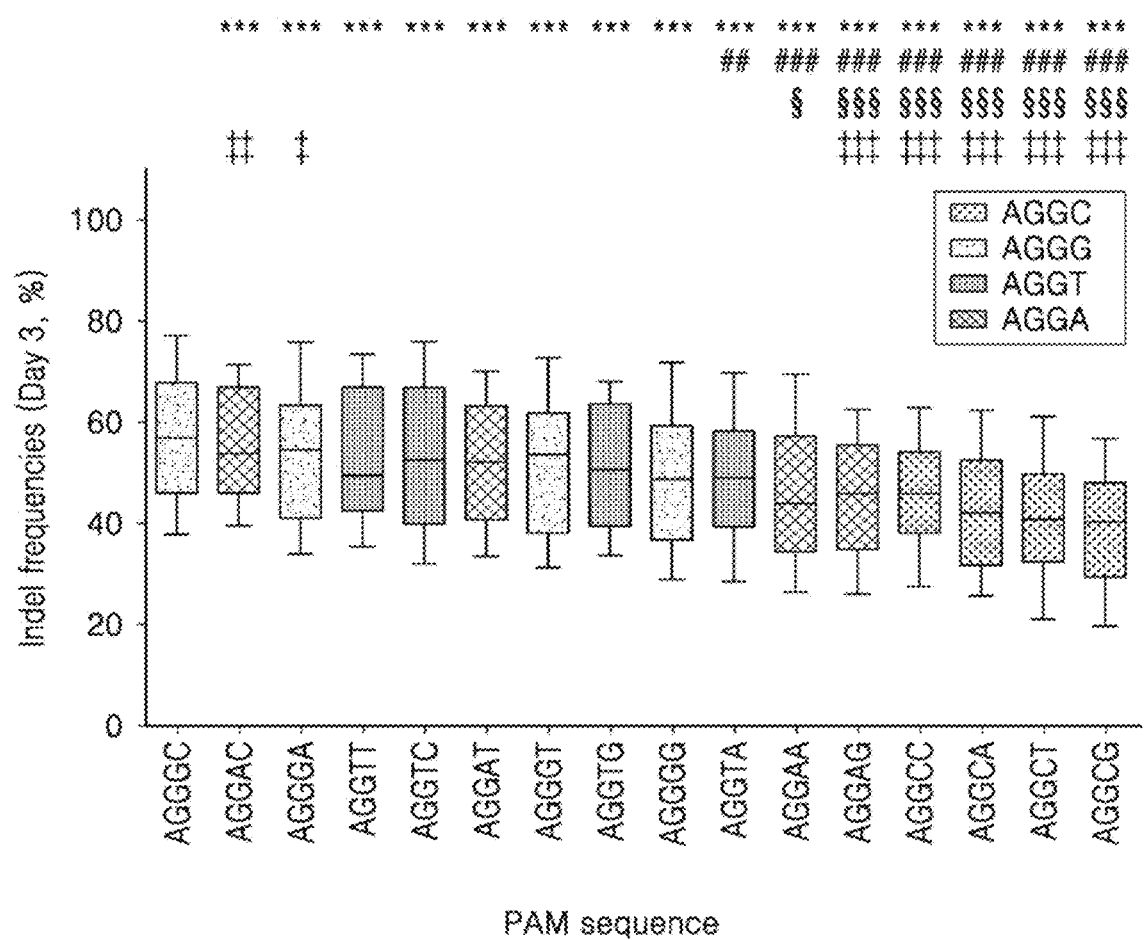
Figure 4A:
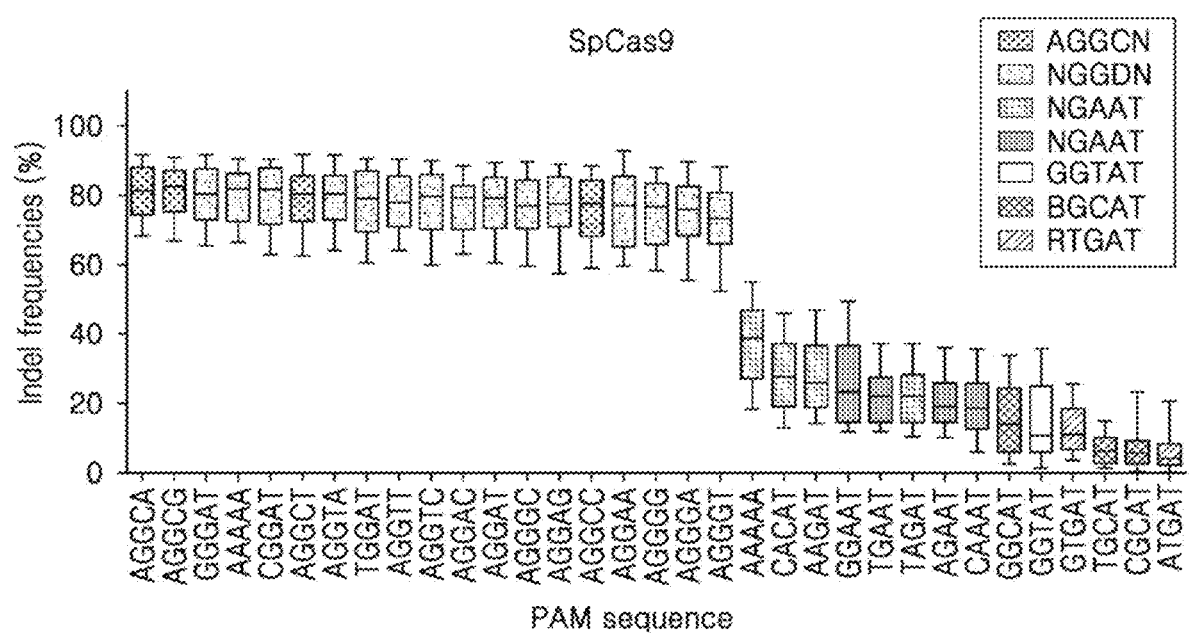
FIGS. 4a, 4b (right panel and left panel) and 4c are graphs showing indel frequencies (%) for PAM sequences for SpCas9 nuclease.
Figure 4B:
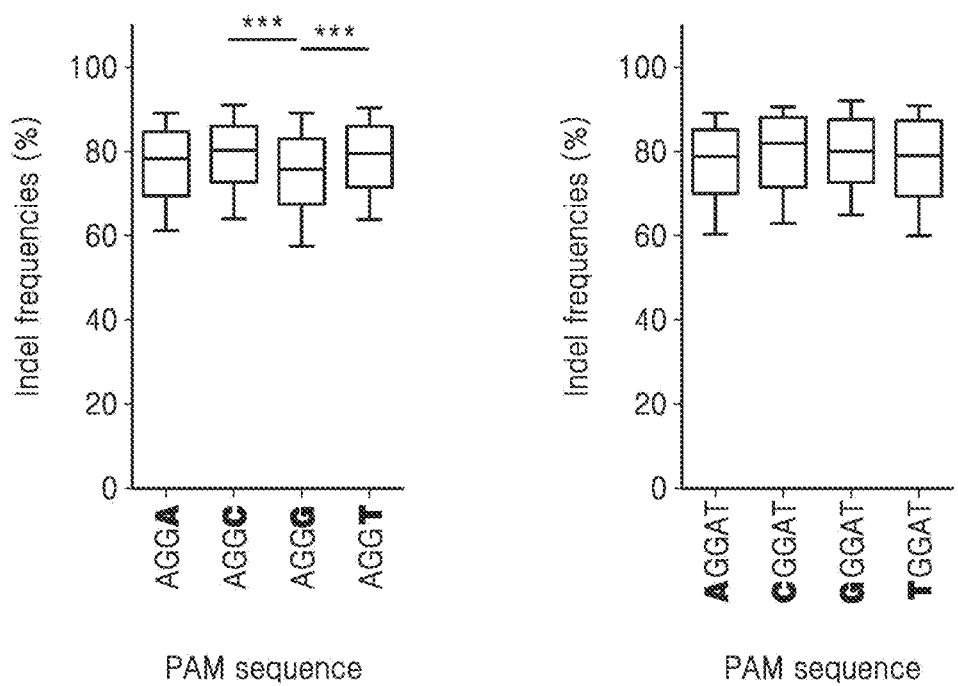
Figure 4C:
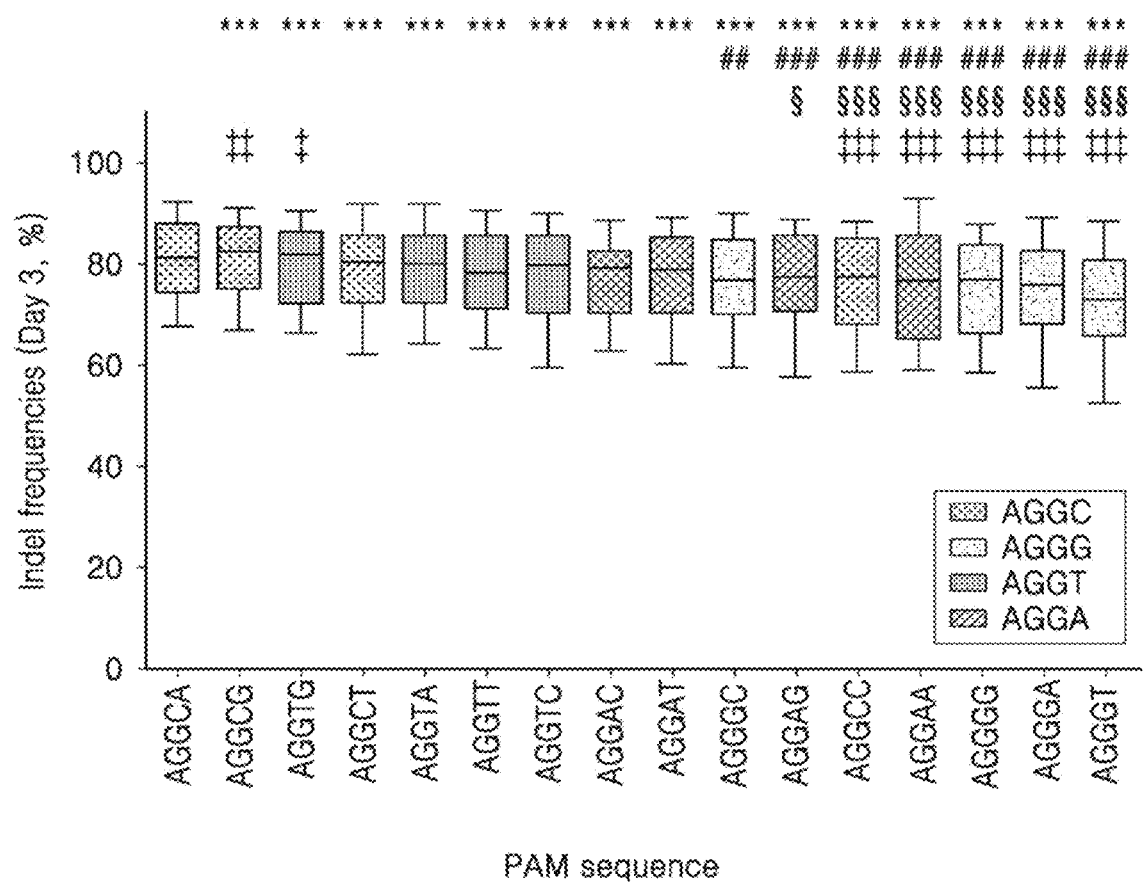

The indel frequencies (%) for xCas9 nuclease and the PAM sequences are shown in FIGS. 2a to 2c; the indel frequencies (%) for SpCas9-NG nuclease and the PAM sequences are shown in FIGS. 3a to 3c; and the indel frequencies (%) for SpCas9 nuclease and the PAM sequences are shown in FIGS. 4a to 4c (ANOVA followed by Tukey's post hoc test; *: P<0.05, : P<0.01, *: P<0.001; ##: P<0.01 and ###: P<0.001 for AGGTC; §: P<0.001 and § § §: P<0.001 for AGGGC; ‡: P<0.05, ‡‡: P<0.01, and ‡‡‡: P<0.001 for AGGAC). The top, middle and bottom lines of the boxes represent the 25th, 50th and 75th percentiles, respectively. The whiskers indicate the 10th and 90th percentiles. N=67 to 79 target sequences per PAM sequence.

As shown in FIGS. 2a to 4c, the PAM sequences were grouped into several groups. For xCas9, SpCas9-NG, and SpCas9 nucleases, the NGG PAM sequence generally exhibited the highest indel frequencies.

xCas9 nuclease significantly induced high indel frequencies at target sequences having, in order of indel frequencies, AGGCA, AGGCB (that is, AGGC(C, G, or T)), or NGGNN PAM sequences (FIGS. 2a to 2c). In addition, six subsets with statistically significant differences were identified. Furthermore, all first, fourth, and fifth nucleotides in the NGGNN PAM sequences affected the xCas9-induced indel frequencies, and xCas9 showed the highest activity when the fourth nucleotide was C (FIGS. 2b and 2c). When the fourth nucleotide was C, the highest xCas9 activity was observed when the fifth nucleotide was A. ii) A nucleotide at the first position that induced the highest xCas9 activity was S (that is, G or C) rather than A. Thus, the most potent xCas9 PAM sequence in this group was predicted to be SGGCA. A representative non-NGG PAM for xCas9 was NGW (that is, NG(A or T)). BGC (or more broadly, NGC) and SAG (or more broadly, NAG) also functioned as PAMs.

In SpCas9-NG, NGT is a non-NGG PAM sequence and exhibited higher indel frequencies than AGGCN PAM, a subset of the NGG PAM sequences (FIG. 3a). Also, the target sequences having an NGGNN (abbreviated as NGGDN) PAM induced significantly higher indel frequencies than those having an AGGCN PAM. Four subsets within the set of the NGGDN PAM sequences associated with statistically significant differences in SpCas9-NG-induced indel frequencies were identified. Only the fourth nucleotide among the first, fourth, and fifth nucleotides in the NGGNN PAM sequences influenced the SpCas9-NG-induced indel frequencies and SpCas9-NG showed high activity when the fourth nucleotide was D (not C) (FIGS. 3b and 3c). A potent non-NGG PAM for SpCas9-NG was NGT. NGA, NGC, NGN, NAG, NAH, NTG, GTH, and VCG also functioned as PAMs.

In contrast to xCas9 and SpCas9-NG, SpCas9 did not exhibit sequential indel frequencies for the NGGDN PAM sequences. All the analyzed NGGDN PAM sequences exhibited similar SpCas9-induced indel frequencies (FIG. 4c). Only the fourth nucleotide among the first, fourth, and fifth nucleotides in the NGGNN PAM sequences influenced the SpCas9-induced indel frequencies and SpCas9 showed high activity when the fourth nucleotide was H (not G) (FIGS. 4b and 4c). A potent non-NGG PAM for SpCas9 was NAG and NGA. GGT, BGC, and RTG also functioned as PAMs.

6. PAM Analysis Using a Wider Range of PAM Sequences and Protospacers

In Example 1.5, 79 PAM sequences were analyzed using 80 fixed, identical protospacer sequences. To analyze PAM sequences more extensively, about 13,200 were prepared from the oligonucleotide library described in Example 1.1.

As described in Examples 1.1 to 1.4, the cell library was prepared from the oligonucleotide library. After Cas9 delivery to the cell library, the indel frequencies were measured. For xCas9, SpCas9-NG, and SpCas9 nucleases, the indel frequencies for the first to fifth nucleotides in the PAM sequences were calculated. The PAM sequences excluded from the analysis are shown as crosshatched in FIGS. 5a to 5c. The number of target sequences per PAM sequence was 3 to 306 (the mean was 33).

Figure 5A:
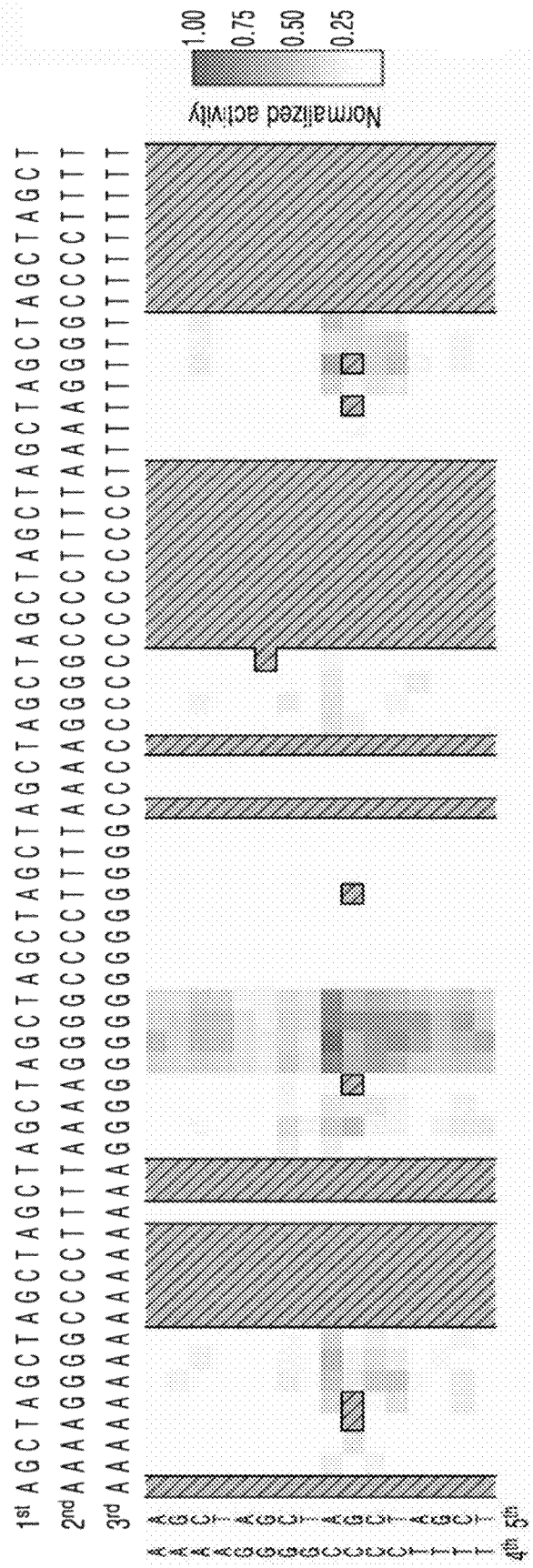
FIGS. 5a to 5c are heat maps showing indel frequencies (%) for 1st to 5th positions in PAM sequences for xCas9, SpCas9-NG, and SpCas9 nucleases, respectively.
Figure 5B:
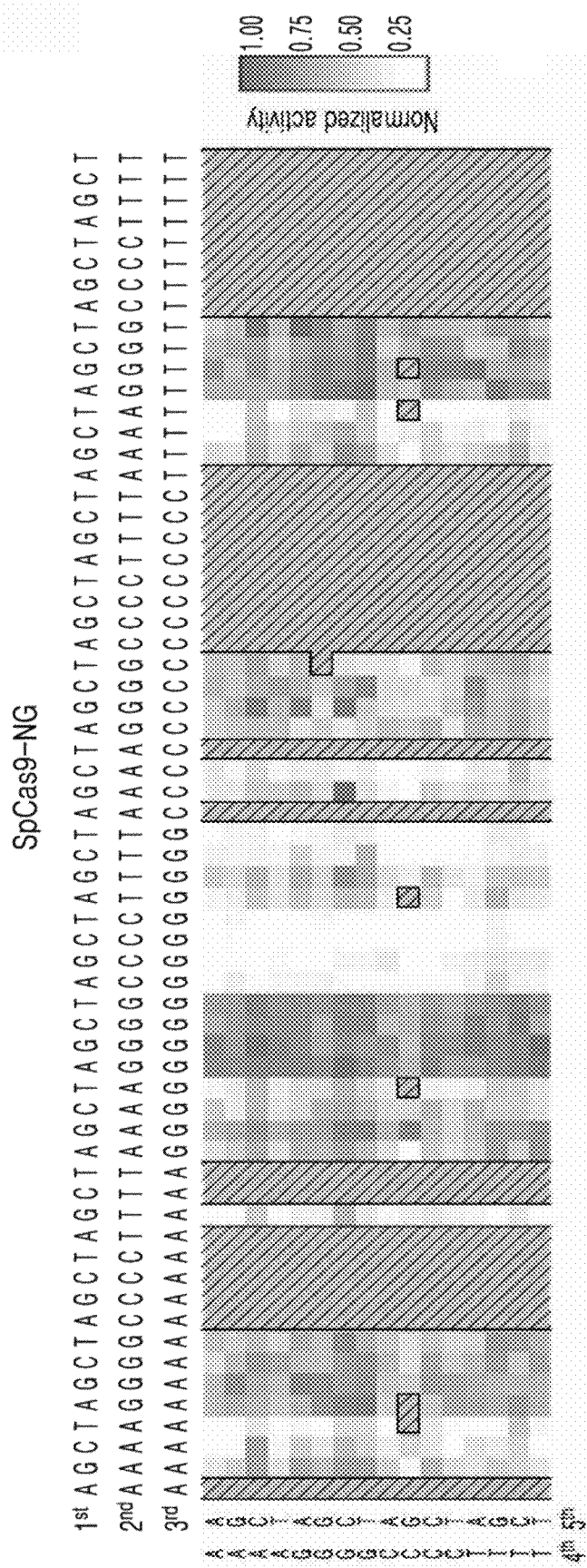
Figure 5C:
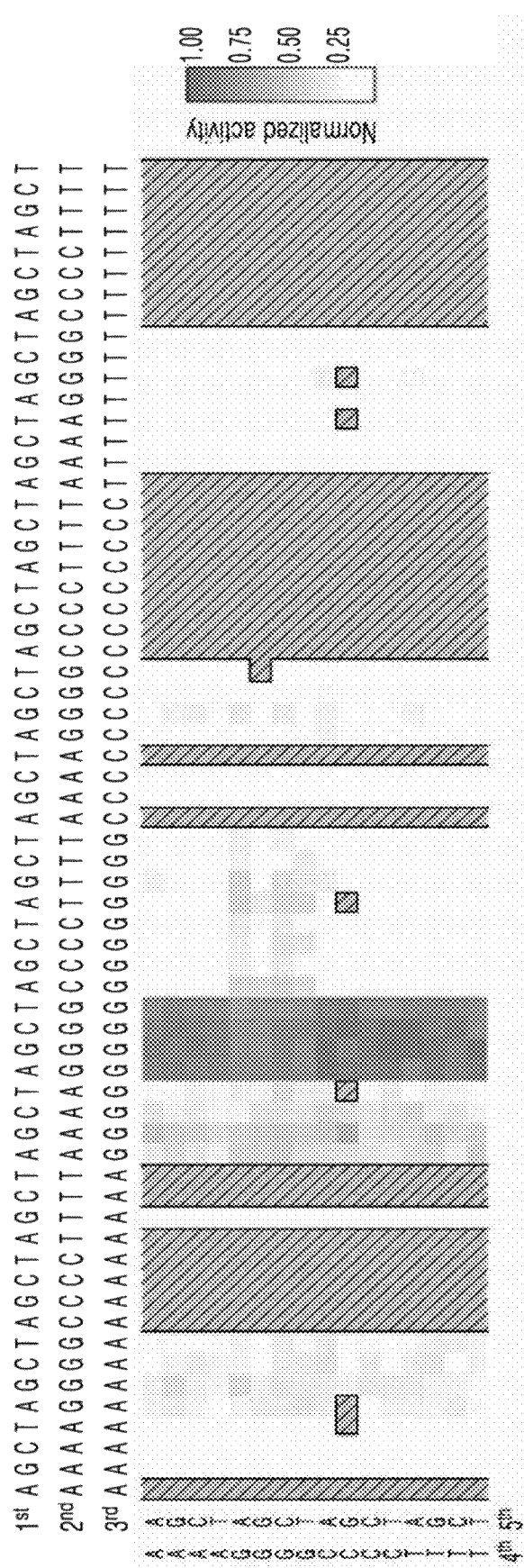
Figure 6A:
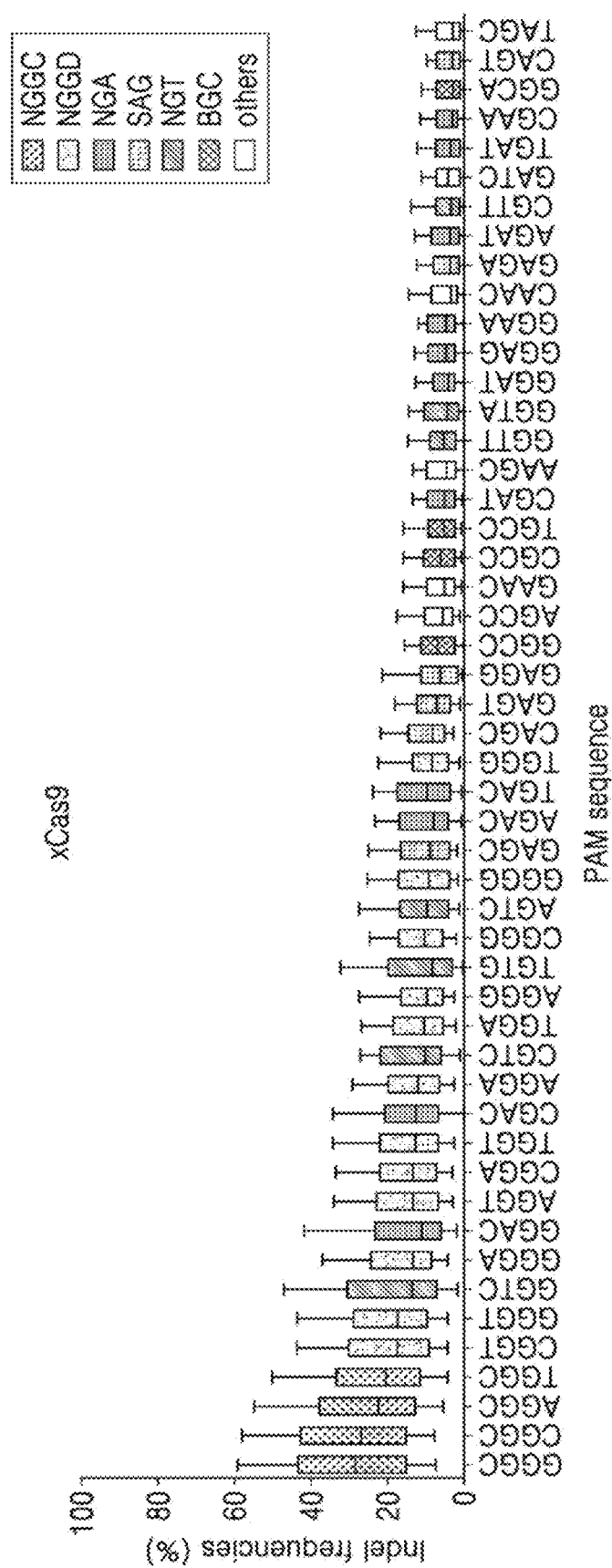
FIGS. 6a to 6c are graphs showing indel frequencies (%) for PAM sequences for xCas9, SpCas9-NG, and SpCas9 nucleases, respectively.
Figure 6B:
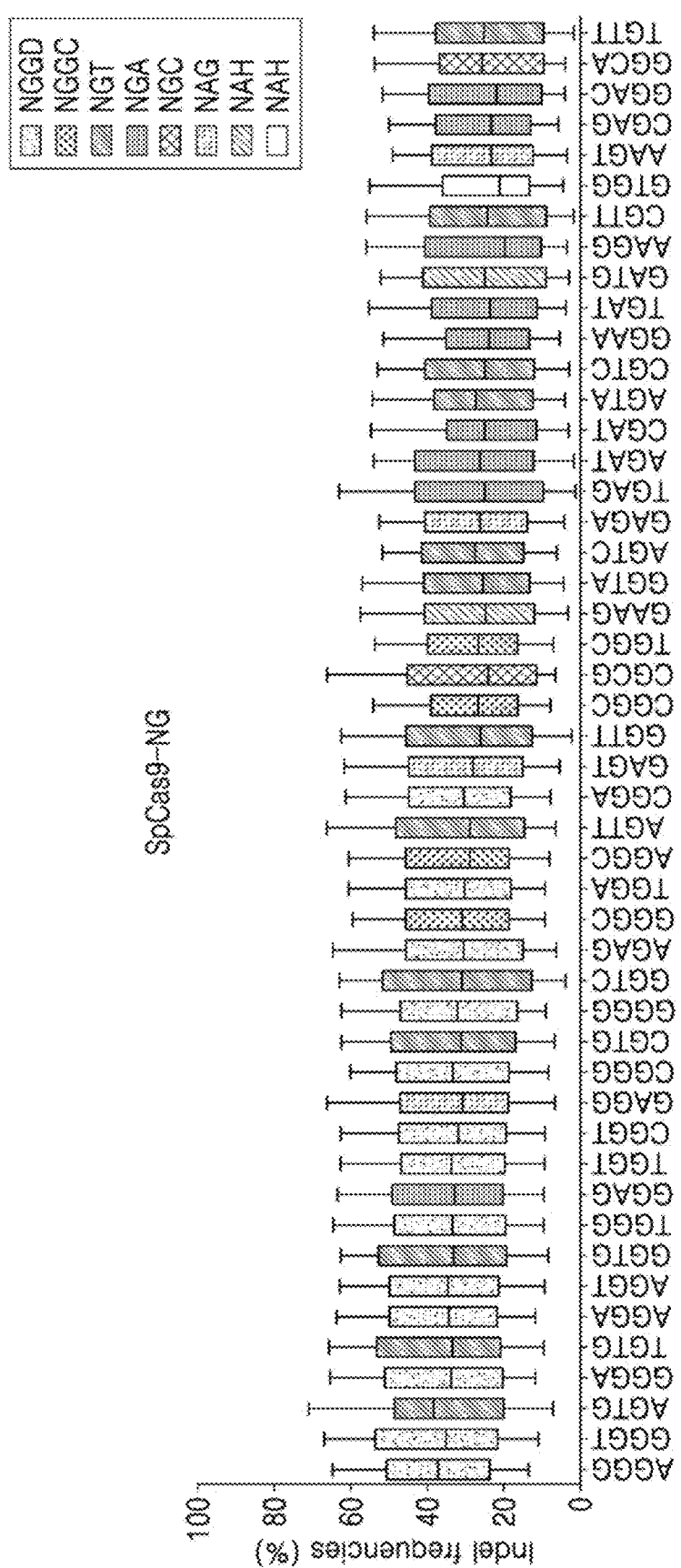
Figure 6C:
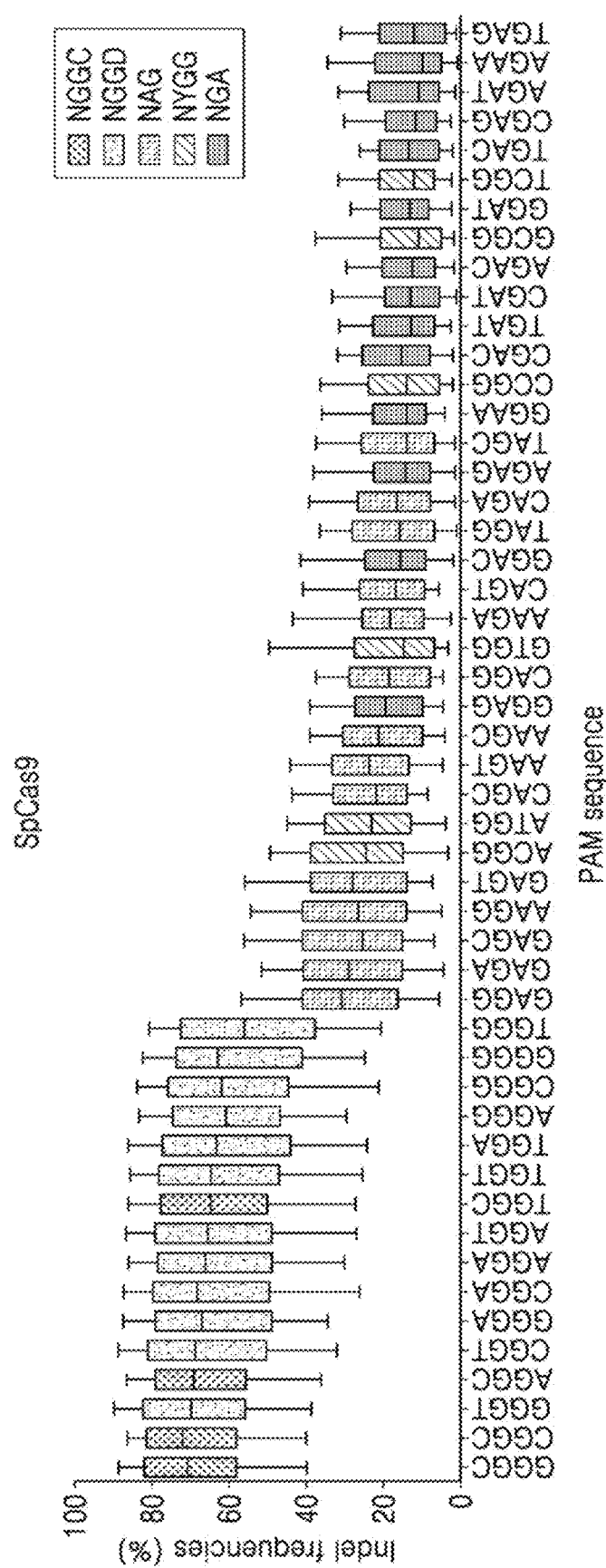
Figure 7A:
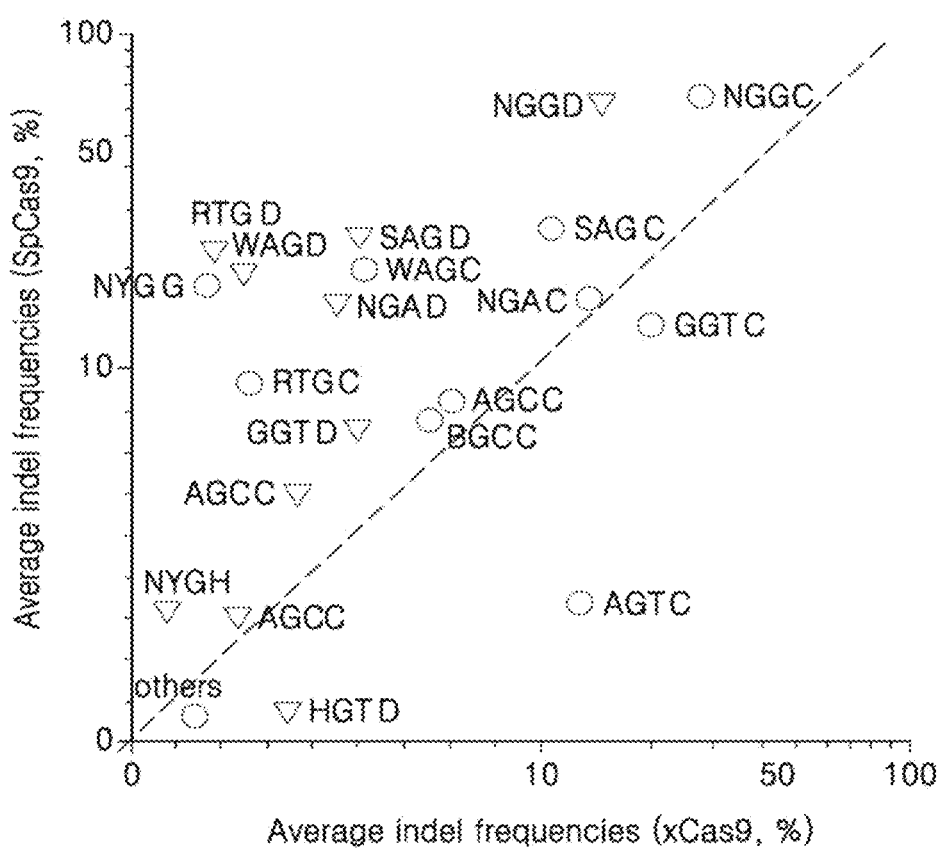
FIGS. 7a to 7c are graphs showing: the average indel frequencies (%) for PAM sequences for xCas and SpCas9; the average indel frequencies (%) for PAM sequences for SpCas9-NG and SpCas9; and the average indel frequencies (%) for PAM sequences for xCas9 and SpCas9-NG, respectively.
Figure 7B:
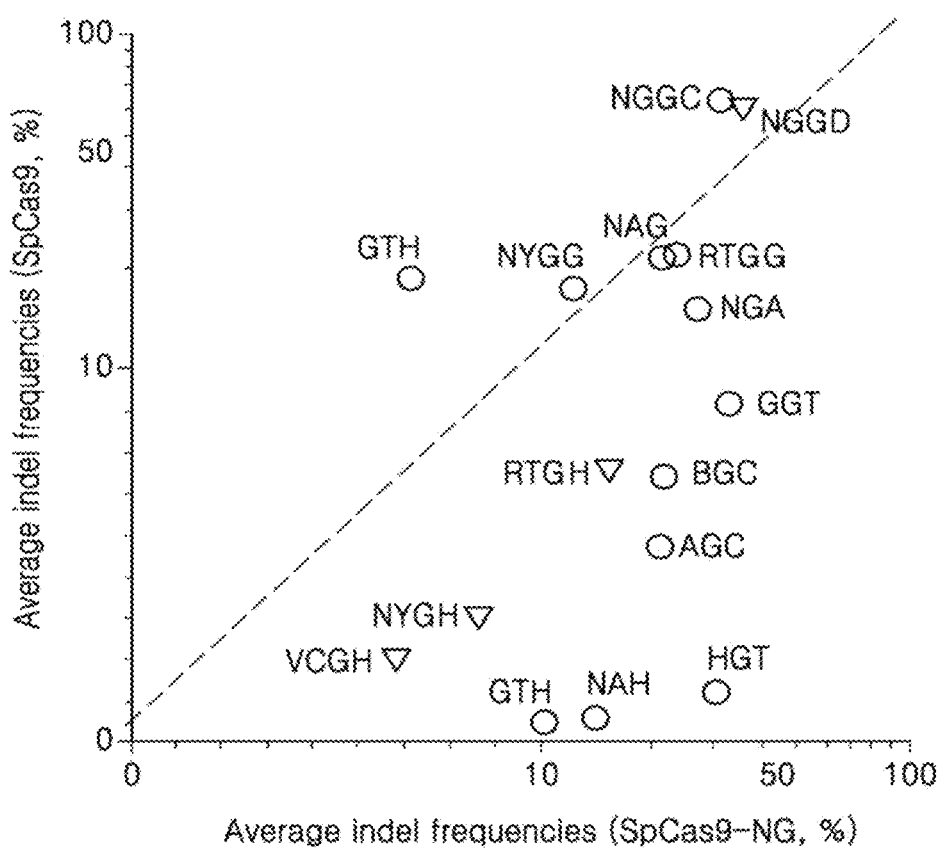
Figure 7C:
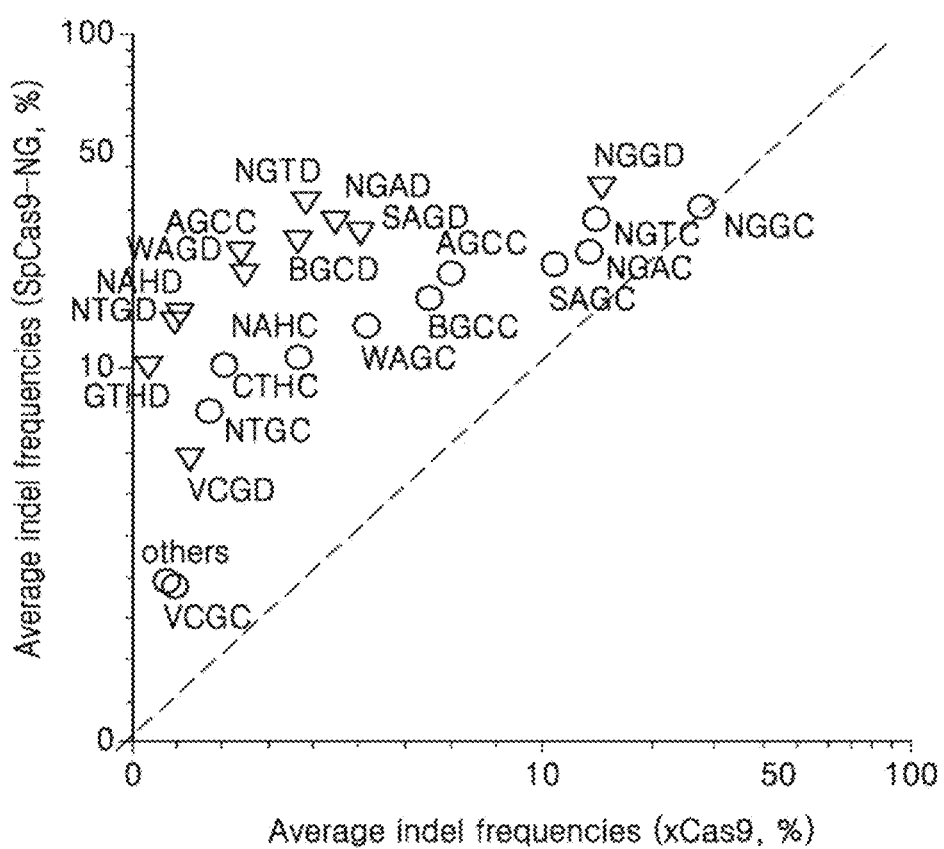

Heat maps showing the indel frequencies (%) for the first to fifth positions in the PAM sequences for xCas9, SpCas9-NG, and SpCas9 nucleases are shown in FIGS. 5a to 5c, respectively. The indel frequencies (%) for the PAM sequences for xCas9, SpCas9-NG, and SpCas9 nucleases are shown in FIGS. 6a to 6c, respectively. Graphs showing the average indel frequencies (%) for the PAM sequences of xCas9 and SpCas9, the average indel frequencies (%) for the PAM sequences of SpCas9-NG and SpCas9, and the average indel frequencies (%) for the PAM sequences of xCas9 and SpCas9-NG are shown in FIGS. 7a to 7c, respectively. In FIGS. 7a to 7c, the dotted line represents y=x. The x-axis and y-axis are shown on a linear scale from 0% to 10% and on a logarithmic scale from 10% to 100%.

592 (=37 3-nt PAM sequences$\times 4^2$) 5-nt PAM sequences include all of the possible PAMs presented in the analysis of Example 1.5. Seven of the 592 PAM sequences were omitted from the analysis due to random selection of target sequences and low sequencing read counts. In the resulting 585 5-nt PAM sequences, the mean of the target sequences per PAM sequence was 33.

As shown in FIGS. 5a and 6a, for xCas9 nuclease, 93 of the top 95 5-nt PAM sequences that showed average indel frequencies higher than 10% were included in the group of NGG, NGW, SAG, and BGC PAMs. The two remaining PAM sequences were AGCCA and CAACG. This result is compatible with a previous finding that AGC and CAA can act as PAMs for xCas9 nuclease in bacterial cells (Hu, J. H. et al, Nature 556, 57-63 (2018)). The PAM sequences that led to the highest average indel frequencies were GGGCA, CGGCA, AGGCA, and TGGCA; they resulted in average indel frequencies of 39%, 34%, 33%, and 32%, respectively, suggesting that (C or G)GGCA are the most potent PAM sequences. Meanwhile, the non-NGG PAM sequences for xCas9 in the top-95 5-nt PAM sequences were NGW, SAG, and BGC, and most of them had C at the fourth nucleotide position, and NGGC, NGWC, SAGC, and BGCC led to higher average indel frequencies compared with NGGD, NGWD, SAGD, and BGCD, respectively. In addition, PAM sequences that led to indel frequencies of 5% or higher, including AGCCA (12%), CAACG (11%), and GAACA (9.7%) were identified. In addition, for xCas9 nuclease, PAM sequences of 5'-NGD-3', 5'-SAG-3', and 5'-BGCC-3' were identified.

As shown in FIGS. 5b and 6b, for SpCas9-NG nuclease, top-455 5-nt PAM sequences that showed average indel frequencies higher than 10% were all included in the group of NGN, NAN, NTG, GTH, and VCG PAMs. In contrast to xCas9, the average SpCas9-NG-induced indel frequencies were lower when the fourth nucleotide was C compared with D (average indel frequencies, 32% for NGND versus 28% NGNC, 17% for NAND versus 13% for NANC, 14% for NTGD versus 8.9% for NTGC, 10% for GTHD versus 10% for GTHC, and 7.5% for VCGD versus 4.2% for VCGC). It was found that TCGDG sequences (average indel frequency: 8.4%) also functioned as PAMs. Also, for SpCas9-NG, novel PAM sequences of 5'-NA-3', 5'-NTG-3', 5'-GTH-3', 5'-VCGD-3', and 5'-TCGDG-3' were identified.

As shown in FIGS. 5c and 6c, for SpCas9 nuclease, 241 of the top-243 5-nt PAM sequences that showed average indel frequencies higher than 10% were included in the group of NGG, NAG, NGA, GGT, BGC, RTG, and NYGG PAMs. The two remaining PAM sequences from the top 243 were AGCCA and CTGCA, and led to insertion frequencies of 16% and 10%, respectively. PAMs in the NGG category ranked from 1 to 64 and were clearly distinguished from the rest, corroborating that NGG is the most effective PAM sequence for SpCas9. In contrast to xCas9 and SpCas9-NG, SpCas9 did not exhibit a preference for specific nucleotides at the fourth position, with the exception of RTG and NYGG. In addition, for SpCas9, 14 PAM sequences, such as AGCCA (16%), CTGCA (10%), TGTCA (8.0%), GCGCA (7.5%), and AGCTC (5.1%), that led to SpCas9-induced indel frequencies higher than 5%, were identified. In addition, for SpCas9, novel PAM sequences of 5'-GGT-3', 5'-BGC-3', 5'-RTG-3', 5'-NYGG-3', 5'-AGCCA-3', 5'-CTGCA-3', 5'-TGTCA-3', 5'-GCGCA-3', 5'-GCGCT-3', 5'-GCGTT-3', 5'-AGCCC-3', 5'-CGTCA-3', 5'-GCGTA-3', 5'-AGCCG-3', 5'-GCGTC-3', 5'-AGTCA-3', 5'-AGCAC-3', and 5'-AGCTC-3' were identified.

As shown in FIGS. 7a to 7c, SpCas9 showed the highest activity for 5'-NGG-3' NGG PAM sequences and xCas9 showed higher activity than SpCas9 for 5'-GGTC-3' and 5'-HGT-3' PAM sequences. SpCas9-NG had higher activity than SpCas9 for most non-NGG PAMs, except for 5'-NYGG-3' and 5'-VCGG-3'. Compared with xCas9, SpCas9-NG showed higher activity for all of the analyzed PAM sequences, except for 5'-NGGC-3'.

Thus, using novel PAM sequences to discover targetable positions in the human genome and predict the indel-inducing activities of nucleases for the PAM sequence could increase the applicability of genome editing.

The invention claimed is:

1. A method for modifying a target nucleic acid in the genome of a cell, the method comprising:
   incubating a cell comprising a target nucleic acid; a polynucleotide encoding a clustered regularly interspaced short palindromic repeats (CRISPR)-associated (Cas) nuclease or a variant thereof, and a guide RNA,
   wherein the Cas nuclease or a variant thereof is *Streptococcus pyogenes* Cas9-NG (SpCas9-NG),
   wherein the target nucleic acid comprises a protospacer adjacent motif (PAM) and a target sequence complementary to the guide RNA,
   the PAM consists of a sequence selected from the group consisting of 5'-NTG-3', 5'-GTH-3', 5'-VCGD-3', and 5-TCGDG-3',
   the target nucleic acid can be recognized by a complex of the Cas nuclease or a variant thereof with the guide RNA, and
   the complex of the Cas nuclease or a variant thereof with the guide RNA modifies the target nucleic acid sequence-specifically.

2. The method of claim 1, wherein the guide RNA is a polynucleotide complementary to a nucleotide sequence having consecutive 2 to 24 nucleotides in the 5'- or 3'-direction of the PAM in the target nucleic acid.

3. The method of claim 1, wherein the length of the guide RNA is 17 to 24 nucleotides.

4. The method of claim 1, wherein the modification is cleavage, insertion, ligation, deamination, or combinations thereof.

* * * * *

SEQUENCE LISTING

<160> NUMBER OF SEQ ID NOS: 11

<210> SEQ ID NO 1
<211> LENGTH: 55
<212> TYPE: DNA
<213> ORGANISM: Artificial Sequence
<220> FEATURE:
<223> OTHER INFORMATION: Forward primer for Oligonucelotide pool
      amplification

<400> SEQUENCE: 1
ttgaaagtat ttcgatttct tggctttata tatcttgtgg aaaggacgaa acacc    55

<210> SEQ ID NO 2
<211> LENGTH: 57
<212> TYPE: DNA
<213> ORGANISM: Artificial Sequence
<220> FEATURE:
<223> OTHER INFORMATION: Reverse primer for Oligonucelotide pool
      amplification

<400> SEQUENCE: 2
gagtaagctg accgctgaag tacaagtggt agagtagaga tctagttacg ccaagct    57

<210> SEQ ID NO 3
<211> LENGTH: 97
<212> TYPE: DNA
<213> ORGANISM: Artificial Sequence
<220> FEATURE:
<223> OTHER INFORMATION: Insert fragment containing the sgRNA scaffold

<400> SEQUENCE: 3
cgtctctgtt ttagagctag aaatagcaag ttaaaataag gctagtccgt tatcaacttg    60

```
aaaaagtggc accgagtcgg tgcttttttg ggagacg                                97
```

<210> SEQ ID NO 4
<211> LENGTH: 56
<212> TYPE: DNA
<213> ORGANISM: Artificial Sequence
<220> FEATURE:
<223> OTHER INFORMATION: Forward primer for 1st PCR reaction

<400> SEQUENCE: 4

```
acactctttc cctacacgac gctcttccga tctcttgaaa aagtggcacc gagtcg         56
```

<210> SEQ ID NO 5
<211> LENGTH: 57
<212> TYPE: DNA
<213> ORGANISM: Artificial Sequence
<220> FEATURE:
<223> OTHER INFORMATION: Forward primer for 1st PCR reaction

<400> SEQUENCE: 5

```
acactctttc cctacacgac gctcttccga tcttcttgaa aagtggcac cgagtcg         57
```

<210> SEQ ID NO 6
<211> LENGTH: 58
<212> TYPE: DNA
<213> ORGANISM: Artificial Sequence
<220> FEATURE:
<223> OTHER INFORMATION: Forward primer for 1st PCR reaction

<400> SEQUENCE: 6

```
acactctttc cctacacgac gctcttccga tctcgcttga aaaagtggca ccgagtcg      58
```

<210> SEQ ID NO 7
<211> LENGTH: 61
<212> TYPE: DNA
<213> ORGANISM: Artificial Sequence
<220> FEATURE:
<223> OTHER INFORMATION: Reverse primer for 1st PCR reaction

<400> SEQUENCE: 7

```
gtgactggag ttcagacgtg tgctcttccg atctttaagt cgagtaagct gaccgctgaa    60
g                                                                      61
```

<210> SEQ ID NO 8
<211> LENGTH: 62
<212> TYPE: DNA
<213> ORGANISM: Artificial Sequence
<220> FEATURE:
<223> OTHER INFORMATION: Reverse primer for 1st PCR reaction

<400> SEQUENCE: 8

```
gtgactggag ttcagacgtg tgctcttccg atctattaag tcgagtaagc tgaccgctga    60
ag                                                                     62
```

<210> SEQ ID NO 9
<211> LENGTH: 63
<212> TYPE: DNA
<213> ORGANISM: Artificial Sequence
<220> FEATURE:
<223> OTHER INFORMATION: Reverse primer for 1st PCR reaction

<400> SEQUENCE: 9

```
gtgactggag ttcagacgtg tgctcttccg atcttattaa gtcgagtaag ctgaccgctg    60
aag                                                                    63
```

```
<210> SEQ ID NO 10
<211> LENGTH: 49
<212> TYPE: DNA
<213> ORGANISM: Artificial Sequence
<220> FEATURE:
<223> OTHER INFORMATION: Forward primer for 2nd PCR reaction

<400> SEQUENCE: 10
aatgatacgg cgaccaccga gatctacaca cactctttcc ctacacgac              49

<210> SEQ ID NO 11
<211> LENGTH: 45
<212> TYPE: DNA
<213> ORGANISM: Artificial Sequence
<220> FEATURE:
<223> OTHER INFORMATION: Reverse primer for 2nd PCR reaction

<400> SEQUENCE: 11
caagcagaag acggcatacg agatgtgact ggagttcaga cgtgt                  45
```